(12) United States Patent
Porubcan (10) Patent No.: US 7,122,370 B2
(45) Date of Patent: Oct. 17, 2006

(54) **FORMULATIONS TO INCREASE *IN VIVO* SURVIVAL OF PROBIOTIC BACTERIA AND EXTEND THEIR SHELF-LIFE**

(76) Inventor: Randolph Stanley Porubcan, 8142 Orchid St., P.O. Box 389, Victoria, MN (US) 55386

( * ) Notice: Subject to any disclaimer, the term of this patent is extended or adjusted under 35 U.S.C. 154(b) by 227 days.

(21) Appl. No.: 10/743,402

(22) Filed: Dec. 22, 2003

(65) Prior Publication Data

US 2004/0175389 A1    Sep. 9, 2004

Related U.S. Application Data

(60) Provisional application No. 60/439,887, filed on Jan. 14, 2003.

(51) Int. Cl.
*C12N 1/04* (2006.01)
*C12N 1/20* (2006.01)
*A61K 39/00* (2006.01)

(52) U.S. Cl. ............... 435/260; 435/252.9; 424/184.1
(58) Field of Classification Search ............ 530/533.5; 435/252.9, 260, 857; 424/184.1
See application file for complete search history.

(56) References Cited

U.S. PATENT DOCUMENTS

| | | | |
|---|---|---|---|
| 4,927,763 A | 5/1990 | Sudoma et al. | |
| 4,956,295 A | 9/1990 | Sudoma | |
| 5,389,532 A | 2/1995 | Divies et al. | |
| 6,033,887 A | 3/2000 | Charpentier | |
| 6,365,148 B1 | 4/2002 | Kim et al. | |
| 6,455,052 B1 | 9/2002 | Marcussen et al. | |
| 6,531,152 B1 | 3/2003 | Lerner et al. | |
| 6,632,457 B1 | 10/2003 | Sawhney | |
| 2003/0165472 A1* | 9/2003 | McGrath et al. | 424/93.4 |

OTHER PUBLICATIONS

Hansen, L.T., et al., Food Microbiology, 19, 35-45, 2002.
Sultana, K., et al., Intl. J. of Food Microbiol., 62, 47-55, 2000.

* cited by examiner

*Primary Examiner*—Lynette R. F. Smith
*Assistant Examiner*—Lakia J. Tongue
(74) *Attorney, Agent, or Firm*—Eric Mirabel (57) ABSTRACT

Disclosed is a formulation for preserving the life of probiotic bacteria during passage through the stomach, while permitting their release in the intestine, and which has a low water activity and correspondingly long shelf life. These formulations are designed to retain potency up to the product expiration date. The formulation includes a substantially water-free mixture of probiotic bacteria with monovalent alginate salts, wherein the mixture has been formed and is maintained in a substantially water-free environment. The alginate salts include sodium alginate and potassium alginate, but not divalent salts such as magnesium alginate or calcium alginate. Generally, an enteric coating (e.g., gelatin or cellulose encapsulation) for the formulation is provided.

14 Claims, 4 Drawing Sheets
(4 of 4 Drawing Sheet(s) Filed in Color)

FORMULATIONS TO INCREASE *IN VIVO* SURVIVAL OF PROBIOTIC BACTERIA AND EXTEND THEIR SHELF-LIFE

RELATED APPLICATIONS

This application claims priority to U.S. Provisional Application Ser. No. 60/439,887, filed Jan. 14, 2003.

BACKGROUND

Dietary supplements containing viable probiotic bacteria are increasing in popularity in the marketplace as their health benefits become recognized. These benefits, in addition to supporting intestinal health and function, include (depending on the bacterial strain selected) repopulating the gut after antibiotic therapy, offsetting lactose intolerance, supporting the immune system and reducing cholesterol. Lactic acid bacteria, primarily from the *Lactobacillus* and *Bifidobacterium* genera, that are capable of improving or maintaining intestinal health and function are termed probiotic bacteria. Probiotic bacteria (referred to herein as probiotics) are sensitive to various environmental conditions such as pH, moisture, temperature, air and light. When these conditions are not properly controlled, the product's viability (measured in colony forming units or cfu), and therefore its efficacy, can be substantially reduced. Products with reduced viability and efficacy have been commercialized, which has contributed to probiotics as a class not achieving the same level of market acceptance as other health supplements.

New generation strains that adhere to intestinal epithelial cells and persist longer in the intestinal tract have appeared in the marketplace in the last few years; these strains are more efficacious compared to strains previously in use (old generation strains). Probiotic companies have isolated new generation strains directly from the intestinal tracts of healthy people rather than from cultured dairy products or other foods, which were common sources for old generation strains. These new, human origin strains are often more sensitive to processing conditions, such as fermentation, concentration and drying and, thus, require special handling in order to survive commercial preparation. Conventional processing techniques, developed largely for old generation strains, are often too harsh for these new generation strains.

Both new and old generation probiotic stains are sensitive to water activity (aw or $a_w$), should be in a dry formulation, and to the low pH levels commonly encountered in gastric juice. A high water activity reduces product shelf-life while low pH will reduce cfus and thereby decrease product efficacy. Exposure of both new and old strains to gastric juice at pH 1.5–2.0 for 90 minutes caused reductions in cfu exceeding 99.99% (see Example 1 below). Thus, when dietary supplements containing these strains are administered in conventional capsules or tablets which degrade quickly in the stomach, most of the probiotic bacteria are killed in the stomach before they reach the intestinal tract, which is where they are expected to exert their beneficial effect. Many probiotic manufacturers recommend a substantial daily dose of 1–20 billion cfu which, apparently, is high enough to compensate for the loss experienced in gastric juice. But such a high overage in dosage adds significant cost and negatively affects marketability.

Water activity ($a_w$) has a direct effect on the shelf-life of probiotic products. Values of $a_w$ of 0.07 or higher can dramatically decrease the shelf-life of probiotics. U.S. Pat. Nos. 4,956,295 and 4,927,763 disclose that when dry probiotic bacteria are blended in certain carriers such as inorganic salts (that adsorb less than 1% water by weight) along with 1 to 5% silica gel or 0.1 to 2% molecular sieve adsorbent, the resulting mixtures have an $a_w$ in the range below 0.30, such as 0.10 to 0.25. To maintain shelf-life, attempts to protect probiotics from pH sensitivity must also take into consideration the $a_w$ of the resulting formulation.

Past attempts to correct the pH sensitivity of probiotics by employing microencapsulation or enteric coating techniques have generally not proved to be protective from pH, and, in most situations, have resulted in deleterious water activities in the treated preparations (e.g., water activities of 0.07 or higher). Microencapsulation and enteric coating techniques involve applying a film forming substance, usually by spraying substances contained in water, onto the dry probiotics. Water should not be used in a post drying treatment of probiotics since the water activity increase will cause a corresponding decrease in shelf-life. And even if the mixture is subsequently dried, the water activity may remain high, as it is extremely difficult to remove water from previously dry probiotics. A high water activity means that the probiotic manufacturer can only guarantee potency at time of manufacture, not at the time of consumption.

SUMMARY

Disclosed is a formulation for preserving the life of probiotic bacteria during passage through the stomach, while permitting their release in the intestine, and which has a low water activity and correspondingly long shelf life. These formulations are designed to retain potency up to the product expiration date. The formulation includes a substantially water-free mixture of probiotic bacteria with monovalent alginate salts, wherein the mixture has been formed and is maintained in a substantially water-free environment. The alginate salts include sodium alginate and potassium alginate, but not divalent salts such as magnesium alginate or calcium alginate. Generally, an enteric coating (e.g., gelatin or cellulose encapsulation) for the formulation is provided.

The formulation can be exposed to pH conditions in the stomach for up to two hours (enough time to permit passage through the stomach to the intestine), without significant bacterial death (as determined by colony forming units, or cfu). While the formulation is resistant to degradation in the acidic environment in the stomach, it will degrade and release the probiotic bacteria in the essentially neutral pH environment in the intestine, where the bacteria can act effectively and not be killed, as they would be in the low pH in the stomach.

The protective effect from monovalent alginates, when directly mixed with dry probiotics and subsequently filled into gelatin or cellulose capsules, appears to be due to such alginate's ability to convert to insoluble alginic acid. Alginic acid forms a gel-like shell that encases the majority of the mixture, holding it in a semi-dry condition at a pH substantially higher than that of the external environment. The gel-structure, looking like a small sausage, forms in the shape of the original capsule and is relatively resistant to disruption or dissolution as long as it remains in an acidic environment. However, when the gel-structure is placed in an environment with a pH>7.0, as encountered in the small intestine, it readily dissolves and releases viable probiotic bacteria, as the insoluble alginic acid is converted back to a soluble alginate salt. Either potassium alginate or sodium alginate, or combination thereof, are suitable for the formulation, but alginate salts of divalent metals such as calcium or magnesium are not suitable, as they are not soluble in water, and thus do not form an alginate gel to protect the probiotics.

It has been found that is both unnecessary and undesirable to utilize sodium alginate as a coating or microencapsulating agent in any process that precedes exposure of the probiotic bacteria to an acidic environment. Commercial and laboratory grades of sodium alginate are not satisfactory for the formulations herein as they contain a significant moisture content that raises the water activity ($a_w$) of blends made with dry probiotics and, consequently, destabilizes them.

Among the processing techniques needed for making the formulations herein are methods of drying sodium alginate that do not adversely affect the water activity when blended with probiotics, but retains the gel forming capability. Another important feature of the mixtures relate to the exceptionally high weight percentage of sodium alginate (10–99% of mixture containing probiotics) that is required to protect the probiotics in gastric juice.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows the outer gel structure and FIG. 1B shows inner gel structure; it can be seen that the internal contents remain dry to semi-dry. The burgundy red color of the exterior of the gel-structure is a result of the pH indicator properties of grape skin extract, an ingredient that turns red in an acidic environment. The internal contents have a lavender color, indicating a higher pH.

DETAILED DESCRIPTION

The objective of the formulations herein are to: 1) produce dry probiotic formulations that are stable and resistant to gastric juice at pH 1.5–2.5; and 2) reduce the water in the production process so it does not reduce the shelf-life of the formulations. The formulations should be prepared in a low humidity room with relative humidity controlled at 20% (+/−5%). One should use a vacuum drier (e.g., LabLine Model #3620, from Lab-Line Instruments, Inc., Melrose Park, Ill.) which is capable of drying powders in trays at temperatures from about 40–70° C., at vacuums ranging from 24–29 inches of Hg. An instrument for measuring water activity in powders should also be used, e.g., the Rotronic Hygromer Model A2 available form Rotronic Instrument Corp., Huntington, N.Y.

The functional percentage of sodium alginate (potassium alginate or other monovalent alginates can also be used) ranges from 10–99% of the total formulation weight, and can be from 15–80%, and may be optimal at 20–60%. The amount of alginate required somewhat depends on the amount of probiotic culture powder used in the formulation, but is largely independent of the number of viable bacteria present, since they occupy an insignificant amount of space. The probiotic bacteria can be used as either freeze-dried or spray dried powders.

The amount of alginate is more dependent on the presence of ingredients other than the probiotic in the formulation, including carriers or other active ingredients. When sodium alginate is used at 20–60% of the formula weight a variety of carrier ingredients including food grade starches, microcrystalline cellulose, anhydrous dextrose, kaolin clay or silica can be used along with the dry probiotics to form the remainder of the formulation. Calcium compounds such as calcium carbonate are not used as carriers since an excess of calcium forms an insoluble gel with sodium alginate that does not dissolve in the intestinal tract. The most important factor in determining the amount of sodium alginate required in the formulation is that it is sufficient to form a stable gel-structure that retains its contents in a dry or semi-dry condition at a pH substantially higher than that of gastric juice when the capsules containing the formulation contact gastric juice. See FIGS. 1 to 4.

The source of sodium alginate may be critical. Sodium alginate is a linear polysaccharide normally isolated from certain species of brown seaweed and algae such as species from the genera *Laminaria* and *Macrocystis*. Because it is the structural component of these algae it has the advantageous property of being strong yet flexible. Sodium alginate is a copolymer that consists of two uronic acids: D-mannuronic acid (M) and L-guluronic acid (G) and as its chemistry is a function of the linkages of M and G, many combinations are possible. Thickening or viscosity effects depend on the molecular weight of the copolymer whereas gelation depends more on the content of glucuronic acid. Both effects may be involved in the process of protecting probiotics in gastric juice.

The specific chemical structure for sodium alginate that is optimal for the formulations herein has not been fully explored. Therefore, sodium alginate from sources other than those used herein (Keltone HV from ISP Technologies, Inc, Wayne, N.J.; Colloid 488 T from Tic Gums, Inc., Belcamp, Md. Keltone HV; and Alginic Acid, Sodium Salt, catalogue numbers A2033 and A7128, Sigma-Aldrich, St. Louis, Mo.) should be empirically tested according to the procedures set out in the examples to determine whether it is acceptable.

Keltone HV is available as a powder with a moisture content of 9–12%. Colloid 488 T is available as a powder with a moisture content up to 15%. Both sodium alginate brands can be directly mixed with the probiotics in a suitable mixer such as a Patterson-Kelly double cone mixer. But when used without alteration of their moisture content, they will significantly reduce the shelf-life (measured as loss of cfu during storage at room temperature) of the probiotics due to high water activity in the resulting mixtures.

The sodium alginate ingredient should be dried prior to mixing with the probiotics to insure that a desirable water activity (0.01 to 0.05) is achieved in the final blend. This water activity level requires that the sodium alginate be dried to between 1–5% moisture content, from a starting moisture content that can be as high as 15% in commercial grades of sodium alginate. Drying must be of a gentle nature to prevent decarboxylation reactions from occurring, as these could negatively affect the viscosity/gelling properties of the alginate copolymer and, thus, its ability to protect probiotics in gastric juice. The best method for drying involves the use of a vacuum oven which can be operated at low temperatures while drawing a vacuum on the product being dried. For purposes of the present invention it is acceptable to dry sodium alginate products at 50–60° C. for 8–24 hours in a vacuum oven operating at a vacuum of 24–29 inches of mercury. Alginates dried in this manner have residual moisture contents of 1–5% and do not negatively impact the water activity when incorporated into blends with probiotics. Optionally, low temperature infrared convection drying can be used to dry the sodium alginate but the temperature should not be allowed to exceed 60° C. or denaturing, decarboxylation reactions may occur.

All drying operations and subsequent handling and blending should be done in a low humidity room with the humidity controlled at 20% (+/−5%). When it is necessary to utilize a separate carrier ingredient(s) in blends containing dry sodium alginate and dry probiotics, that ingredient(s) should have a water activity in the range of 0.01 to 0.05 or be dried accordingly to achieve such a range. Acceptable carrier ingredients include food starches with moisture contents below 3%, anhydrous dextrose and microcrystalline cellulose, e.g., Avicel PH112, which has a moisture content of 1.5%. Accurate water activity measurements demand careful attention to procedure, as indicated in the instruction manual for the Rotronic Hygromer Model A2.

All ingredients, including the probiotic culture powder(s), should test within the water activity range of 0.01–0.05. Ingredients are weighed to their required weights in a humidity controlled room at 20% (+/−5%) relative humidity and may be blended under similar conditions in a Patterson-Kelly type twin cone blender. Such a blender imparts minimum shear to powders during blending. After blending the product is hermetically sealed in steel drums until it can be encapsulated into capsules (e.g., gelatin or cellulose) which step should also be carried out in a low humidity room.

By keeping sodium alginate in dry admixture with probiotics at low water activity and in gelatin or cellulose capsules, the product remains stable with a reasonable shelf-life. Upon exposure to gastric juice (after consumption) the sodium alginate reconstitutes and forms a sausage shaped gel-structure composed of alginic acid, which quickly becomes impervious to liquids and, thereby, protects the ingredients contained within it allowing these ingredients to remain dry or semi-dry at a pH orders of magnitude higher than that of the surrounding gastric juice. It is likely that the sodium alginate also serves as a pH buffer during this process and helps to maintain the higher internal pH. The gelatin or cellulose capsules serve as a mold for the sausage shape of the alginic acid gel-structure. The sausage shaped gel-structure remains in the absence of the capsule, which quickly dissolves and disappears. The thickness of the shell or wall of the gel-structure varies from 5–30% of its diameter depending on the characteristics of the particular formulation.

Figure 1A:
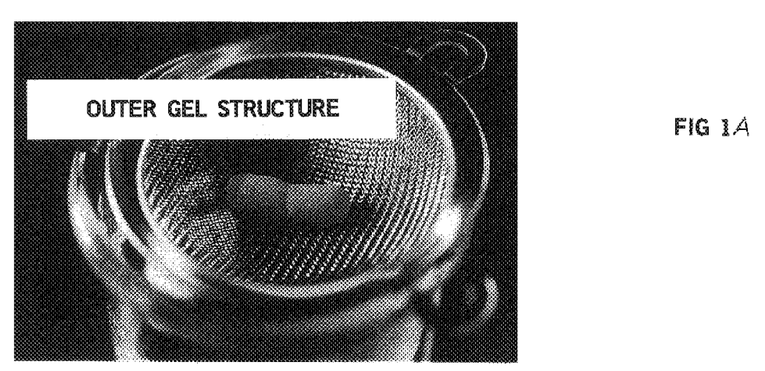
FIGS. 1A and 1B show photographs of the sausage shaped gel-structures that form in solution using the alginates described herein.
Figure 1B:
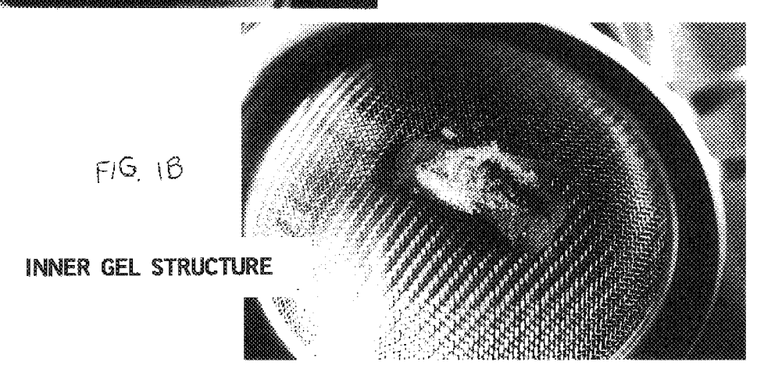
Figure 2:
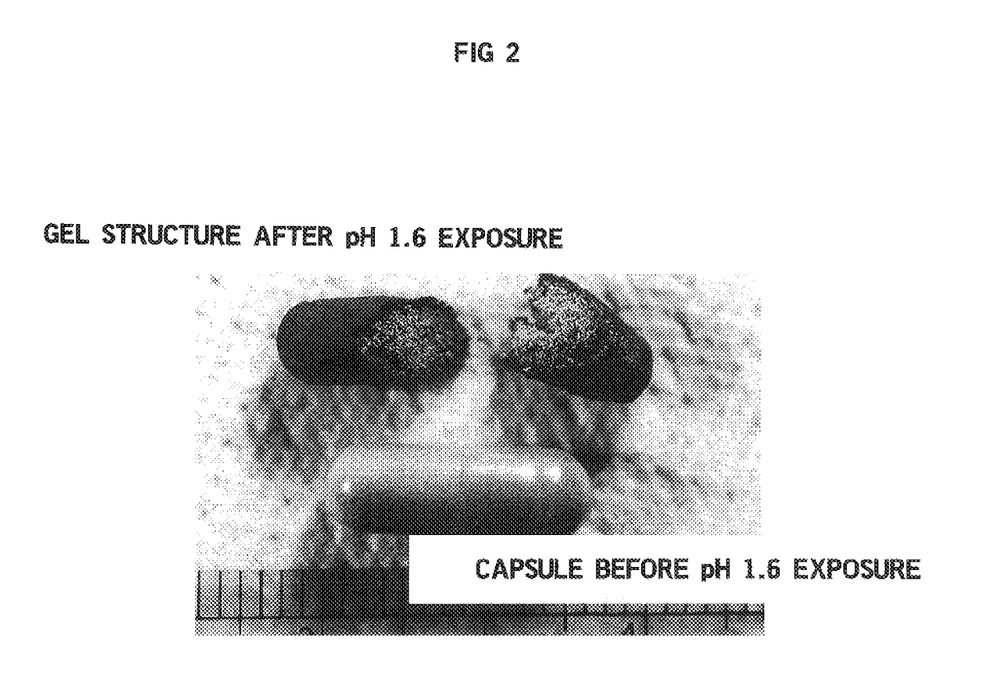
FIG. 2 shows a gel structure that formed after submersion in pH 1.6 (simulated gastric juice) for 90 minutes; cut open to reveal both the external shell and the semi-dry internal contents. A capsule prior to exposure to pH 1.6 (lower) is shown for comparison.
Figures 3A, 3B, 3C:
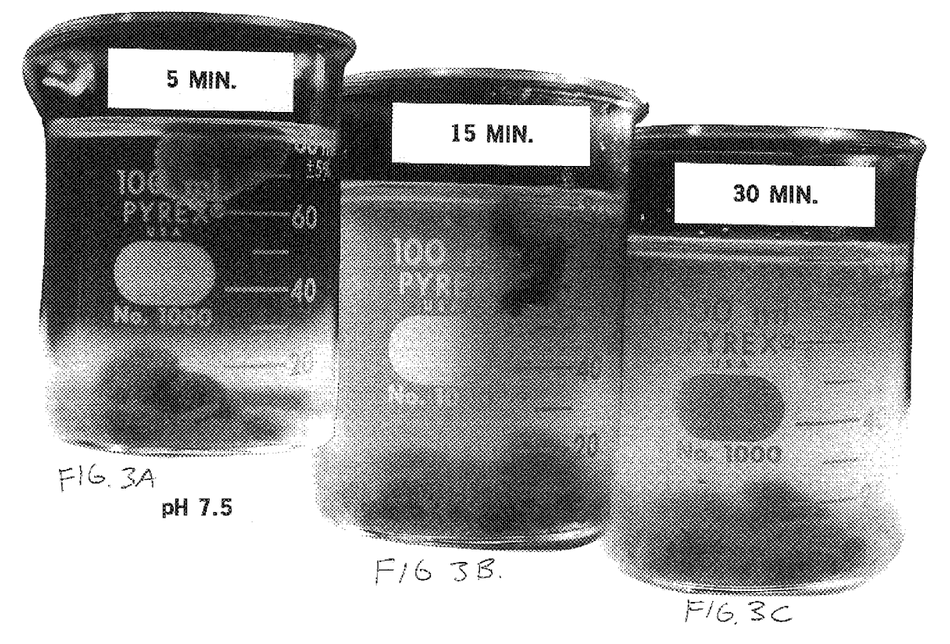
FIGS. 3A, 3B and 3C show, respectively, photographs of three beakers containing the gel-structures in pH 7.5 buffer, simulating conditions in the small intestine. It can be seen that the gel-structures disperse and dissolve readily, at this higher pH. This dissolving action results when the alginic acid shell of the gel-structure reverts to a soluble alginate salt.
Figure 4:
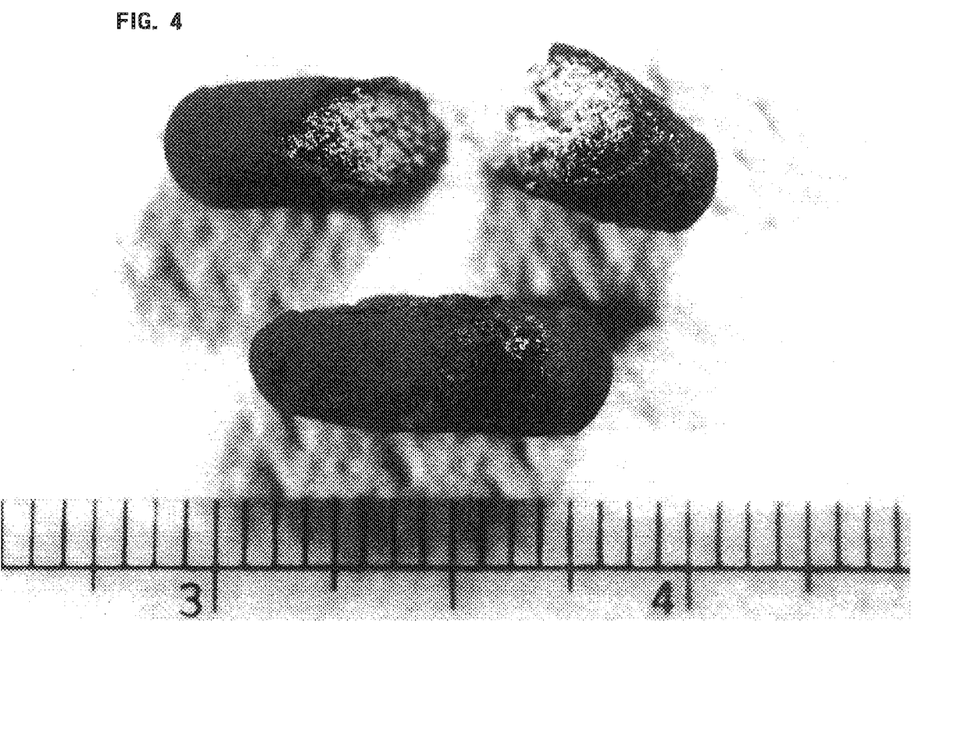
FIG. 4 shows an enlarged photograph of a whole and cut open gel-structure with a scale in inches shown at the bottom.

Upon entering an alkaline pH environment such as the small intestine, the gel-structure readily disperses and dissolves and releases the probiotic bacteria (see FIG. 3).

In addition to probiotics, sodium alginate and inert carriers, grape skin extract powder can be added to the formulations. Grape skin extract contains bioflavonoid antioxidants (anthocyanins) which protect probiotic bacteria from oxidation and further improve their shelf-life. Formulations used in the examples of the present invention contain 5% grape skin extract (AC 12z WSP Grape Skin Extract Powder, Chr. Hansen, Inc. West Allis, Wis.). During the research that lead to the present invention it was discovered that grape skin extract exhibits another effect that has commercial value. Grape shin extract serves as a unique, natural, pH indicator when used at 1–10% of the formulation weight and produces a lavender colored powder that changes to burgundy-red in gastric juice at pH 1.5–2.5. This causes the shell or wall of the protective gel-structures to turn burgundy-red (indicating acid pH) while the inner contents stay lavender or becomes blue-purple (indicating alkaline pH). This feature allows practitioners and sales professionals to visually demonstrate the formulation's characteristics and effectiveness.

The examples below demonstrate several features of the formulations described herein. Four commercial, freeze-dried probiotic cultures were used to demonstrate the effectiveness of the formulations herein on new generation probiotics: 1) *Lactobacillus paracasei* strain F-19 from Medipharm, Inc., Des Moines, Iowa.; 2) *Lactobacillus rhamnosus* HOWARU strain HN001 from Danisco A/S, Brabrand, Denmark; 3) *Bifidobacterium lactis* HOWARU strain HN019 from Danisco A/S, Brabrand Denmark; and 4) *Bifidobacterium bifidum* strain BB-12 from Chr. Hansen A/S, Horsholm, Denmark, and two old generation probiotic cultures are also used: *Lactobacillus acidophilus* strain LA-1 from Chr. Hansen, Inc., West Allis, Wis. and *Lactobacillus casei* strain 163 from Danisco, Milwaukee, Wis. The above cultures are only representative examples, however, as the formulations and methods herein can be used for all probiotic species and strains, including those within the *Lactobacillus* and *Bifidobacterium* genera, e. g., the following:

Exemplary *Lactobacillus* Species and Strains:

*Lactobacillus acidophilus, Lactobacillus amylovorus. Lactobacillus bulgaricus, Lactobacillus casei, Lactobacillus delbrueckii, Lactobacillus fermentum, Lactobacillus gasseri, Lactobacillus helveticus, Lactobacillus johnsonii, Lactobacillus lactis, Lactobacillus paracasei, Lactobacillus pentosaceus, Lactobacillus plantarum, Lactobacillus reuteri, Lactobacillus rhamnosus*, and *Lactobacillus salivarius*, Exemplary *Bifidobacterium* Species and Strains:

*Bifidobacterium animalis, Bifidobacterium bifidum, Bifidobacterium breve, Bifidobacterium infantis, Bifidobacterium lactis, Bifidobacterium longum.*

EXAMPLE I

Demonstration of Probiotic Viability Reduction by Simulated Gastric Juice

Six *Lactobacillus* probiotic cultures were added to simulated gastric juice (made from 2.0 gm sodium chloride+3.2 gm pepsin+7.0 ml hydrochloric acid+distilled water to make 1,000 ml, pH=1.6) to produce a concentration of $1 \times 10^8$ cfu/ml. Each culture was tested separately. The mixtures were held at 37° C. for 90 minutes and then immediately plated on MRS agar (Oxoid, CM 361). The mixture was incubated in anaerobic jars for 72 hours at 37° C. The viable plate counts in cfu are reported in TABLE 1.

TABLE 1

| $10^8$ cfu/ml @ T = 0 | cfu/ml after 90 min. at pH 1.6/37° C. |
|---|---|
| Lactobacillus paracasei strain F-19 | <$10^4$ |
| Lactobacillus rhamnosus strain HN001 | <$10^4$ |
| Bifidobacterium lactis strain HN019 | 5 × $10^5$ |
| Bifidobacterium bifidum strain BB-12 | 2 × $10^6$ |
| Lactobacillus acidophilus strain LA-1 | <$10^4$ |
| Lactobacillus casei strain 163 | <$10^4$ |

Conclusion: Exposure to simulated gastric juice at pH 1.6 for 90 minutes dramatically reduces the viable plate count (in cfu) of all cultures tested.

EXAMPLE 2

EXAMPLE 2

Demonstration of Dry Probiotic's Sensitivity to Water Activity

The freeze-dried probiotic cultures as in Example 1 were mixed as follows: A Blend: 10 grams culture powder+70 grams microcrystalline cellulose (Avicel PH112, FMC Corp.)+20 grams Colloid 488 T (14% moisture); B Blend: Same as A Blend except that Colloid 488 T was dried in a vacuum oven at 50° C. for 8 hours to 3.2% moisture. The average water activity for the A-Blends was 0.12 and for the B-Blends, 0.045. The mixed cultures were stored in amber glass bottles at 25° C. for 90 days, and plate counts were made on MRS agar as in Example 1 at T=0 and at T=90 days. The results are set forth below in TABLE 2.

TABLE 2

| | A-Blends<br>$a_w$ = 0.12<br>T = 0 cfu/T = 90 cfu | B-Blends<br>$a_w$ = 0.045<br>T = 0 cfu/T = 90 cfu |
|---|---|---|
| Lactobacillus paracasei strain F-19 | 20 × $10^9$/10 × $10^7$ | 20 × $10^9$/16 × $10^8$ |
| Lactobacillus rhamnosus strain HN001 | 10 × $10^9$/5 × $10^6$ | 10 × $10^9$/9 × $10^8$ |
| Bifidobacterium lactis strain HN019 | 57 × $10^9$/3 × $10^7$ | 57 × $10^9$/33 × $10^8$ |
| Bifidobacterium bifidum strain BB12 | 82 × $10^9$/2 × $10^8$ | 82 × $10^9$/78 × $10^8$ |
| Lactobacillus acidophilus strain LA1 | 42 × $110^9$/4 × $10^5$ | 42 × $110^9$/32 × $10^8$ |
| Lactobacillus casei strain 163 | 160 × $10^9$/24 × $10^9$ | 160 × $10^9$/155 × $10^9$ |

Conclusion: With the possible exception of *L. casei* 163, a water activity of 0.12 dramatically reduces probiotic shelf-life at 25° C., as compared with a water activity of 0.045.

EXAMPLE 3

Preparation of Formulations

Preparation of Batch A

Keltone HV brand sodium alginate was dried in a vacuum oven at 55° C. for 8 hours from an initial moisture content of 9% to a moisture content of 3.2%. Subsequently, the following mixture was produced in a lab scale double-cone mixer with all ingredients added by weight percent: 20% vacuum dried Keltone HV, 63% microcrystalline cellulose (Avicel PH112, FMC Bioploymer), 10% freeze-dried *Lactobacillus paracasei* strain F-19 (200 billion cfu/gram, Medipharm, Inc.), 5% grape skin extract (AC 12z WSP, Chr. Hansen, Inc.), 2% silica (Syloid 63, W. R. Grace & Co.). The ingredients were blended at 60 rpm for 10 minutes until uniformly lavender in color from the grape skin extract. The resulting powder was hand filled into 50 size "0" cellulose capsules (Vcaps, Capsugel) at 300 mg per capsule and 50 size "0" gelatin capsules at 310 mg per capsule. The resulting blend, prior to filling capsules, had a water activity of 0.045 measured on a Rotronic Model A2 Hygromer. All operations were carried out in a low humidity room (20% relative humidity). The resulting capsules were stored in amber glass bottles at 25° C., tightly closed, with silica gel packets for moisture absorption.

Preparation of Batch B

The same procedure was followed as for BATCH A except the Keltone HV was not vacuum dried, it was used at 9% moisture content as received form the manufacturer and, as such, was added to the mixture at 20% by weight. The water activity of this mixture measured 0.10.

Testing Procedures

Shelf-Life

Capsules from BATCH A & B were stored for 90 days at 25° C. in their respective glass bottles, tightly closed; both gelatin and cellulose capsules were tested. The capsules were plated on MRS agar (Oxoid CM361) at time T=0 (start of shelf-life test) and at T=90 days; the plates were incubated at 37° C. for 72 hours in an anaerobic jar (approximately 90% hydrogen, 10% CO2). Plates containing between 30–300 colonies were counted and the respective counts were reported in colony forming units (cfu)/gram.

Stability in pH 1.6 Simulated Gastric Juice

Ten capsules of each type were submersed in pH 1.6 simulated gastric juice (2.0 g sodium chloride+3.2 g pepsin+7.0 ml HCl+distilled water to make 1 liter) for 90 minutes. After 90 minutes the capsule contents (sausage shaped gel-structures) were rinsed thoroughly with distilled water and partially dried on a paper towel for 15 minutes. The quality of the resulting sausage shaped gel-structures were rated on a quality index scale of 1 to 5:1=little or no surviving gel-structure, capsule contents mostly spilled out into the gastric juice; 2=poor quality gel-structure with minimal sausage shape and internal contents largely exposed to gastric juice; 3=satisfactory sausage shaped gel-structure with some penetration of gastric juice into internal contents, burgundy-red outside, dark purple with some wetness inside; 4=Good quality sausage shaped gel-structure with some swelling, intact and dry to semi-dry inside, burgundy-red outside, lavender colored inside; 5=excellent sausage shaped gel-structure, completely intact and dry inside, burgundy-red outside, lavender inside.

The viable plate count and pH of the contents of the sausage structures were determined after the 15 minute drying time (note: this determination is only possible for sausage structures having a quality index of 3 or better). Five capsules from each test (BATCH A, gelatin vs cellulose capsules; BATCH B, gelatin vs cellulose capsules) were mashed in 25 ml of sterile distilled water and then checked for pH and plated on MRS agar.

Results—Shelf-Life

TABLE 3

*Lactobacillus paracasei* Formulations

|  | Gelatin Capsules cfu/cap. at T = 0 | Cellulose Capsules cfu/cap. at T = 0 |
|---|---|---|
|  | cfu/cap. at T = 90 Days | cfu/cap. at T = 90 Days |
| BATCH A | $6.2 \times 10^9$ | $6.0 \times 10^9$ |
| (aw = 0.045) | $4.2 \times 10^9$ | $5.3 \times 10^9$ |
| BATCH B | $6.2 \times 10^9$ | $6.0 \times 10^9$ |
| (aw = 0.10) | $4.4 \times 10^7$ | $5.1 \times 10^7$ |

Conclusion: BATCH A (aw=0.045) prepared with vacuum dried (55° C., 8 hrs.) Keltone HV and microcrystalline cellulose (inert carrier) produces a blend with *Lactobacillus paracasei* strain F-19 that is significantly more stable to storage at 25° C. than BATCH B (aw=0.10) prepared with Keltone HV as received from the manufacturer.

Results—Stability in pH 1.6 Gastric Juice

TABLE 4

*Lactobacillus paracasei* Formulations

|  | Gelatin capsules | Cellulose Capsules |
|---|---|---|
| BATCH A |  |  |
| Sausage Gel-Structure Index = | 4 | 4 |
| Internal Contents pH = | 3.9 | 3.8 |
| Internal Contents cfu/cap = | $5 \times 10^2$ | $5.5 \times 10^2$ |
| BATCH B |  |  |
| Sausage Gel-Structure Index = | 4 | 4 |
| Internal Contents pH = | 3.9 | 3.9 |
| Internal Contents cfu/cap = | $5.2 \times 10^2$ | $5.4 \times 10^2$ |

Conclusion: Either source of Keltone HV used at 20%, vacuum dried or as received from the manufacturer, produces an equal stabilizing effect in gastric juice with comparable gel-structures, internal pHs, and cfus/capsule. The cfu survival of *Lactobacillus paracasei* strain F-19 in this example is orders of magnitude greater, as compared with Example 1, where no sodium alginate was in the formulation. The initial plate counts per capsule prior to exposure to gastric juice were $6.2 \times 10^9$ for the gelatin capsules and $6.0 \times 10^9$ for the cellulose capsules.

EXAMPLE 4

Preperation of Formulations

Batch C

Colloid 488T brand sodium alginate was dried in a vacuum oven at 55° C. for 12 hours from an initial moisture content of 15% to a moisture content of 4.2%. Subsequently, the following mixture was produced in a lab scale double-cone mixer with all ingredients added by weight percent: 20% vacuum dried Colloid 488T, 63% potato starch (Perfectamyl D6, Avebe), 10% freeze-dried *Bifidobacterium lactis* strain HN019 (570 billion cfu/gram, Danisco A/S), 5% grape skin extract (AC 12z WSP, Chr. Hansen, Inc.), 2% silica (Syloid 63, W.R. Grace & Co.). The ingredients were blended at 60 rpm for 10 minutes until uniformly lavender in color from the grape skin extract. The resulting powder was hand filled into 50 size "0" cellulose capsules (Vcaps, Capsugel) at 300 mg per capsule and 50 size "0" gelatin capsules at 310 mg per capsule. The resulting blend, prior to filling capsules, had a water activity of 0.049 measured on a Rotronic Model A2 Hygromer. All operations were carried out in a low humidity room (20% relative humidity). The resulting capsules were stored in amber glass bottles at 25° C., tightly closed, with silica gel packets for moisture absorption.

Batch D

The same procedure as for BATCH A was followed except the Colloid 488T was not vacuum dried, it was used at 15% moisture content as received form the manufacturer and was included, as such, at 20% by weight in the blend. The water activity of this blend measured 0.12.

Testing Procedures

The procedures were the same as in EXAMPLE 3.

Results—Shelf-Life

TABLE 5

*Bifidobacterium lactis* Formulations

|  | Gelatin Capsules cfu/cap. at T = 0 | Cellulose Capsules cfu/cap. at T = 0 |
|---|---|---|
|  | cfu/cap. at T = 90 Days | cfu/cap. at T = 90 Days |
| BATCH C | $17.7 \times 10^9$ | $17.1 \times 10^9$ |
| (aw = 0.049) | $9 \times 10^9$ | $14 \times 10^9$ |
| BATCH D | $17.7 \times 10^9$ | $17.1 \times 10^9$ |
| (aw = 0.12) | $2 \times 10^4$ | $4.1 \times 10^7$ |

Conclusion: BATCH C (aw=0.049) prepared with vacuum dried (55° C., 12 hrs.) Colloid 488T and potato starch (inert carrier) produces a blend with *Bifidobacterium lactis* strain HN019 that is significantly more stable to storage at 25° C. than BATCH B (aw=0.12) prepared with Colloid 488T, as received from the manufacturer.

Results—Stability in pH 1.6 Gastric Juice

TABLE 6

*Bifidobacterium lactis* Formulations

|  | Gelatin capsules | Cellulose Capsules |
|---|---|---|
| BATCH C |  |  |
| Sausage Gel-Structure Index = | 4 | 4 |
| Internal Contents pH = | 3.9 | 3.9 |
| Internal Contents cfu/cap = | $15 \times 10^{-2}$ | $16 \times 10^{-2}$ |
| BATCH D |  |  |
| Sausage Gel-Structure Index = | 4 | 4 |
| Internal Contents pH = | 3.8 | 3.9 |
| Internal Contents cfu = | $14 \times 10^{-2}$ | $15 \times 10^{-2}$ |

Conclusion: Either source of Colloid 488T used at 20% by weight, vacuum dried or as received from the manufacturer, produces an equal stabilizing effect in gastric juice with comparable gel-structures, internal pHs, and cfus/capsule. When compared to results from Example 1, the cfu survival of *Bifidobacterium lactis* strain HN019 in this example is orders of magnitude greater. The initial plate counts per capsule prior to exposure to gastric juice were $17.7 \times 10^9$ for the gelatin capsules and $17.1 \times 10^9$ for the cellulose capsules.

EXAMPLE 5

Preperation of Formulation

Batch E

Keltone HV brand sodium alginate was dried in a vacuum oven at 60° C. for 16 hours from an initial moisture content of 9% to a moisture content of 2.9%. Subsequently, the following mixture was produced in a lab scale double-cone mixer with all ingredients added by weight percent: 60% vacuum dried Keltone HV, 23% microcrystalline cellulose (Avicel PH112, FMC Biopolymer), 10% freeze-dried *Lactobacillus rhamnosus* strain HN001 (100 billion cfu/gram, Danisco A/S), 5% grape skin extract (AC 12z WSP, Chr. Hansen, Inc.), and 2% silica (Syloid 63, W.R. Grace & Co.). The ingredients were blended at 60 rpm for 10 minutes until uniformly lavender in color from the grape skin extract. The resulting powder was hand filled into 50 size "0" cellulose capsules (Vcaps, Capsugel) at 300 mg per capsule and 50 size "0" gelatin capsules at 310 mg per capsule. The resulting blend, prior to filling capsules, had a water activity of 0.028 measured on a Rotronic Model A2 Hygromer. All operations were carried out in a low humidity room (20% relative humidity). The resulting capsules were stored in amber glass bottles at 25° C., tightly closed, with silica gel packets for moisture absorption.

Testing Procedures

The procedures were the same as in EXAMPLE 3.

Results—Shelf-Life

TABLE 7

*Lactobacillus rhamnosus* Formulation

|  | Gelatin Capsules cfu/cap. at T = 0 cfu/cap. at T = 90 Days | Cellulose Capsules cfu/cap. at T = 0 cfu/cap. at T = 90 Days |
|---|---|---|
| BATCH E (aw = 0.028) | $3.1 \times 10^9$ $2.5 \times 10^9$ | $3.0 \times 10^9$ $3.0 \times 10^9$ |

Conclusion: This blend containing 60% vacuum dried (16 hour drying time at 60° C. compared to 8 hrs at 55° C. in EXAMPLE 3) Keltone HV produces a very stable mixture with *Lactobacillus rhamnosus* strain HN001. The additional drying time and higher alginate percentage (60% vs 20%) produces a significantly lower water activity (0.028) compared to EXAMPLE 3 (aw=0.045).

Results—Stability in pH 1.6 Gastric Juice

TABLE 8

*Lactobacillus rhamnosus* Formulation

| BATCH E | Gelatin capsules | Cellulose Capsules |
|---|---|---|
| Sausage Gel-Structure Index = | 5 | 5 |
| Internal Contents pH = | 4.0 | 4.1 |
| Internal Contents cfu = | $2.8 \times 10^9$ | $3.0 \times 10^9$ |

Conclusion: The inclusion of 60% vacuum dried Keltone HV produces sausage shaped gel-structures with a quality index of 5, an internal pH of 4.0–4.1, and essentially no significant loss in cfu/capsule over the testing time at pH 1.6.

EXAMPLE 6

Preparation of Formulation

Batch F

Keltone HV brand sodium alginate was dried in a vacuum oven at 60° C. for 16 hours from an initial moisture content of 9% to a moisture content of 2.9%. Subsequently, the following mixture was produced in a lab scale double-cone mixer with all ingredients added by weight percent: 20% vacuum dried Keltone HV, 63% microcrystalline cellulose (Avicel PH112, FMC Biopolymer), 2.5% freeze-dried *Lactobacillus rhamnosus* strain HN001 (100 billion cfu/gram, Danisco A/S), 2.5% freeze-dried *Bifidobacterium lactis* strain HN019 (570 billion cfu/gram, Danisco), 5.0% *Lactobacillus paracasei* strain F-19 (200 billion cfu/gram, Mediphram), 5% grape skin extract (AC 12z WSP, Chr. Hansen, Inc.), 2% silica (Syloid 63, W.R. Grace & Co.). The ingredients were blended at 60 rpm for 10 minutes until uniformly lavender in color from the grape skin extract. The resulting powder was hand filled into 50 size "0" cellulose capsules (Vcaps, Capsugel) at 300 mg per capsule. The resulting blend, prior to filling capsules, had a water activity of 0.038 measured on a Rotronic Model A2 Hygromer. All operations were carried out in a low humidity room (20% relative humidity). The resulting capsules were stored in amber glass bottles at 25° C., tightly closed, with silica gel packets for moisture absorption.

Testing Procedures

The procedures were the same as in EXAMPLE 3.

Results—Shelf-Life

TABLE 9

Three Strain Probiotic Blend Cellulose Capsules

| | cfu/capsule at T = 0 | cfu/capsule at T = 90 days |
|---|---|---|
| BATCH F (aw = 0.038) | $9.0 \times 10^9$ | $7.8 \times 10^9$ |

Conclusion: This blend of three new generation probiotic strains produces very acceptable shelf-life results that compare well to the results obtained when each of the strains are tested individually as in EXAMPLES 3–5.

Results—Stability in pH 1.6 Gastric Juice

TABLE 10

| BATCH F | Three Strain Probiotic Blend Cellulose Capsules |
|---|---|
| Sausage Gel-Structure Index = | 4 |
| Internal Contents pH = | 4.0 |
| Internal Contents cfu = | $8 \times 10^9$ |

Conclusion: This blend of three new generation probiotic strains is protected as well as when the strains are tested individually as in EXAMPLES 1–3.

EXAMPLE 7

Preparation of Formulation

Batch G

Keltone HV brand sodium alginate was dried in a vacuum oven at 60° C. for 16 hours from an initial moisture content of 9% to a moisture content of 2.9%. Subsequently, the following mixture was produced in a lab scale double-cone mixer with all ingredients added by weight percent: 10% vacuum dried Keltone HV, 73% microcrystalline cellulose (Avicel PH112, FMC Biopolymer), 2.5% freeze-dried *Lactobacillus rhamnosus* strain HN001 (100 billion cfu/gram, Danisco A/S), 2.5% freeze-dried *Bifidobacterium lactis* strain HN019 (570 billion cfu/gram, Danisco), 5.0% *Lactobacillus paracasei* strain F-19 (200 billion cfu/gram, Medipharm), 5% grape skin extract (AC 12z WSP, Chr. Hansen, Inc.), 2% silica (Syloid 63, W.R. Grace & Co.). The ingredients were blended at 60 rpm for 10 minutes until uniformly lavender in color from the grape skin extract. The resulting powder was hand filled into 50 size "0" cellulose capsules (Vcaps, Capsugel) at 300 mg per capsule. The resulting blend, prior to filling capsules, had a water activity of 0.044 measured on a Rotronic Model A2 Hygromer. All operations were carried out in a low humidity room (20% relative humidity). The resulting capsules were stored in amber glass bottles at 25° C., tightly closed, with silica gel packets for moisture absorption.

Testing Procedures

The procedures were the same as in EXAMPLE 3.

Results—Shelf-Life

TABLE 11

Three Strain Probiotic Blend

Cellulose Capsules

| | cfu/capsule at T = 0 | cfu/capsule at T = 90 days |
|---|---|---|
| BATCH G (aw = 0.044) | $9.0 \times 10^9$ | $7.4 \times 10^9$ |

Conclusion: Using Keltone HV at 10% by weight in the three strain probiotic blend does not significantly change the shelf-life compared to EXAMPLE 6 where Keltone HV was used at 20%.

Results—Stability in pH 1.6 Gastric Juice

TABLE 12

Three Strain Probiotic Blend

| BATCH G | Cellulose Capsules |
|---|---|
| Sausage Gel-Structure Index = | 3 |
| Internal Contents pH = | 2.9 |
| Internal Contents cfu = | $4 \times 10^8$ |

Conclusion: This blend of three new generation probiotic strains is not protected against simulated gastric juice as well by 10% Keltone HV as it is by 20% Keltone HV in EXAMPLE 6.

EXAMPLE 8

Preparation of Formulation

Batch H

The formulation here is the same as set out in EXAMPLE 7 for BATCH G with the exception that 1% magnesium stearate and 1% stearic acid are added and the amount of microcrystalline cellulose is reduced by 2%. Here BATCH H is not filled into capsules but compressed into 300 mg round tablets using standard pharmaceutical techniques.

Testing Procedures

The procedures were the Same as in EXAMPLE 3.

Results—Shelf-Life

TABLE 13

| Three Strain Probiotic Blend | | |
|---|---|---|
| | 300 mg Tablets | |
| | cfu/tablet at T = 0 | cfu/tablet at T = 90 days |
| BATCH H (aw = 0.046) | $1.5 \times 10^9$ | $9.2 \times 10^8$ |

Conclusion: The stress of tableting caused a greater reduction in initial count compared to encapsulating in gelatin or cellulose capsules. A greater reduction in shelf-life at 90 days was observed compared to capsules.

Results—Stability in pH 1.6 Gastric Juice

TABLE 14

| Three Strain Probiotic Blend | |
|---|---|
| BATCH H | 300 mg Tablets |
| Round Gel-Structure Index = | 3.5 |
| Internal Contents pH = | 3.2 |
| Internal Contents cfu = | $7 \times 10^8$ |

Conclusion: This blend of three new generation probiotic strains is not protected as well in tablets as in gelatin or cellulose capsules but protection is still substantial when compared to unprotected probiotics as demonstrated in Example 1.

The present invention includes many variations, modifications and alterations of the embodiments and methods described above, and the scope of the invention in not defined or limited by the specification or by the examples, but is defined only in the claims that follow, and includes all equivalents of the subject matter of the claims. The steps in the methods set forth below can be practiced in the sequence provided or out of sequence, and are still within the scope of the claims.

What is claimed is:

1. A formulation comprising probiotic bacteria with monovalent alginate salts, wherein the formulation has a water activity of between 0.01–0.07, and wherein, upon exposure to an acidic environment, an alginic acid gel is formed which shields the probiotic bacteria from the antibiotic effects of the acidic environment.

2. The formulation of claim 1 which does not include alginate salts of divalent metals, in quantities such that the shielding alginic acid gel does not form.

3. The formulation of claim 1 wherein the water activity is 0.028 or less.

4. The formulation of claim 1 wherein the monovalent alginate salts are sodium alginate or potassium alginate.

5. The formulation of claim 1 wherein the probiotic bacteria is from the *Lactobacillus* or *Bifidobacterium* genera.

6. The formulation of claim 1 wherein the formulation reacts with acidic environment to generate alginic acid.

7. The formulation of claim 1 which is encapsulated and wherein the encapsulated material is made of gelatin or cellulose.

8. The formulation of claim 7 wherein the capsule materials do not include any alginates salts in them.

9. The formulation of claim 1 wherein the alginate salt is dried to a moisture content below 5% prior to mixing with probiotic bacteria.

10. The formulation of claim 7 wherein the probiotic bacteria are present at a concentration of $10^7$ to $10^{11}$ cfu per capsule.

11. The formulation of claim 3 wherein the weight ratio of sodium alginate in the formulation is 10–99%.

12. The formulation of claim 10 wherein the weight ratio of sodium alginate in the formulation is 20% to 60%.

13. The formulation of claim 1 including grapeskin extract.

14. The formulation of claim 2 wherein the alginate salts of divalent metals are magnesium alginate or calcium alginate.

* * * * *